(12) United States Patent
Owens et al.

(10) Patent No.: US 6,406,721 B1
(45) Date of Patent: Jun. 18, 2002

(54) SALVE FOR TREATING BURNS

(76) Inventors: Wentzel W. Owens, 349 E. Main St., Whiteland, IN (US) 46184; Ansil White; Charles Farley, both of 5581 S. Hasse Town Rd., Morgantown, IN (US) 46160

( * ) Notice: Subject to any disclaimer, the term of this patent is extended or adjusted under 35 U.S.C. 154(b) by 0 days.

(21) Appl. No.: 09/887,233

(22) Filed: Jun. 22, 2001

(51) Int. Cl.7 .......................... A61K 35/78; A61K 31/74
(52) U.S. Cl. ..................... 424/725; 424/78.06; 514/969
(58) Field of Search .............................. 424/725, 78.06; 514/969

(56) References Cited

U.S. PATENT DOCUMENTS 377,978 A * 12/1888 Banks

FOREIGN PATENT DOCUMENTS

JP 58170447 * 10/1983

OTHER PUBLICATIONS

Phytochemical Dictionary: A Handbook of Bioactive Compounds from Plants (1999), edited by Harborne et al., Taylor & Francis, UK, p. 405.*
The Complete Illustrated Herbal: A Safe and Practical Guide to Making and Using Herbal Remedies by Hoffman (1996), Barnes & Noble, Inc., Italy, p. 103.*
http://www.viable-herbal. com/herbdecsc2/1hydrang.htm, "Hydrangea", last updated Nov. 15, 2001.*

* cited by examiner

*Primary Examiner*—Christopher R. Tate
*Assistant Examiner*—Michele C. Flood

(57) ABSTRACT

A salve for treating burns for reducing pain and scarring to burned skin. The salve for treating burns includes combining 3 parts of pork fat with 2 parts of chopped Hydrangea plant by weight to form a mixture. Heating the mixture at a temperature of 175 degrees Celsius until the Hydrangea plant has turned brown. Straining the mixture to define a strained mixture. Cooling the strained mixture to a temperature less than 35 degrees Celsius such that the strained mixture solidifies.

6 Claims, 1 Drawing Sheet

SALVE FOR TREATING BURNS

BACKGROUND OF THE INVENTION

1. Field of the Invention

The present invention relates to salves for healing injuries and more particularly pertains to a new salve for treating burns for reducing pain and scarring to burned skin.

2. Description of the Prior Art

The use of salves for healing injuries is known in the prior art. More specifically, salves for healing injuries heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 4,405,604; U.S. Pat. No. 4,459,285; U.S. Pat. No. 4,837,019; U.S. Pat. No. 5,733,884; U.S. Pat. No. 5,756,107; and U.S. Pat. No. 5,198,217.

While these devices fulfill their respective, particular objectives and requirements, the aforementioned patents do not disclose a new salve for treating burns. The inventive method includes combining 3 parts of pork fat with 2 parts of chopped hydrangea plant by weight to form a mixture. Heating the mixture at a temperature of 175 degrees Celsius until the hydrangea plant has turned brown. Straining the mixture to define a strained mixture. Cooling the strained mixture to a temperature less than 35 degrees Celsius such that the strained mixture solidifies.

In these respects. the salve for treating burns according to the present invention substantially departs from the conventional concepts and designs of the prior art, and in so doing provides an apparatus primarily developed for the purpose of reducing pain and scarring to burned skin.

SUMMARY OF THE INVENTION

In view of the foregoing disadvantages inherent in the known types of salves for healing injuries now present in the prior art, the present invention provides a new salve for treating burns construction wherein the same can be utilized for reducing pain and scarring to burned skin.

The general purpose of the present invention, which will be described subsequently in greater detail, is to provide a new salve for treating burns apparatus and method which has many of the advantages of the salves for healing injuries mentioned heretofore and many novel features that result in a new salve for treating burns which is not anticipated, rendered obvious, suggested, or even implied by any of the prior art salves for healing injuries, either alone or in any combination thereof.

To attain this, the present invention generally comprises combining 3 parts of pork fat with 2 parts of chopped hydrangea plant by weight to form a mixture. Heating the mixture at a temperature of 175 degrees Celsius until the hydrangea plant has turned brown. Straining the mixture to define a strained mixture. Cooling the strained mixture to a temperature less than 35 degrees Celsius such that the strained mixture solidifies.

There has thus been outlined, rather broadly, the more important features of the invention in order that the detailed description thereof that follows may be better understood, and in at order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new salve for treating burns apparatus and method which has many of the advantages of the salves for healing injuries mentioned heretofore and many novel features that result in a new salve for treating burns which is not anticipated, rendered obvious, suggested, or even implied by any of the prior art salves for healing injuries, either alone or in any combination thereof.

It is another object of the present invention to provide a new salve for treating burns which may be easily and efficiently manufactured and marketed.

It is a further object of the present invention to provide a new salve for treating burns which is of a durable and reliable construction.

An even further object of the present invention is to provide a new salve for treating burns which is susceptible of a low cost of manufacture with regard to both materials and labor, and which accordingly is then susceptible of low prices of sale to the consuming public, thereby making such salve for treating burns economically available to the buying public.

Still vet another object of the present invention is to provide a new salve for treating burns which provides in the apparatuses and methods of the prior art some of the advantages thereof, while simultaneously overcoming some of the disadvantages normally associated therewith.

Still another object of the present invention is to provide a new salve for treating burns for reducing pain and scarring to burned skin.

Yet another object of the present invention is to provide a new salve for treating burns which includes combining 3 parts of pork fat with 2 parts of chopped hydrangea plant by weight to form a mixture. Heating the mixture at a temperature of 175 degrees Celsius until the hydrangea plant has turned brown. Straining the mixture to define a strained mixture. Cooling the strained mixture to a temperature less than 35 degrees Celsius such that the strained mixture solidifies.

Still yet another object of the present invention is to provide a new salve for treating burns that is simple and cost effective to make.

These together with other objects of the invention, along with the various features of novelty which characterize the invention, are pointed out with particularity in the claims annexed to and forming a part of this disclosure. For a better understanding of the invention, its operating advantages and the specific objects attained by its uses reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
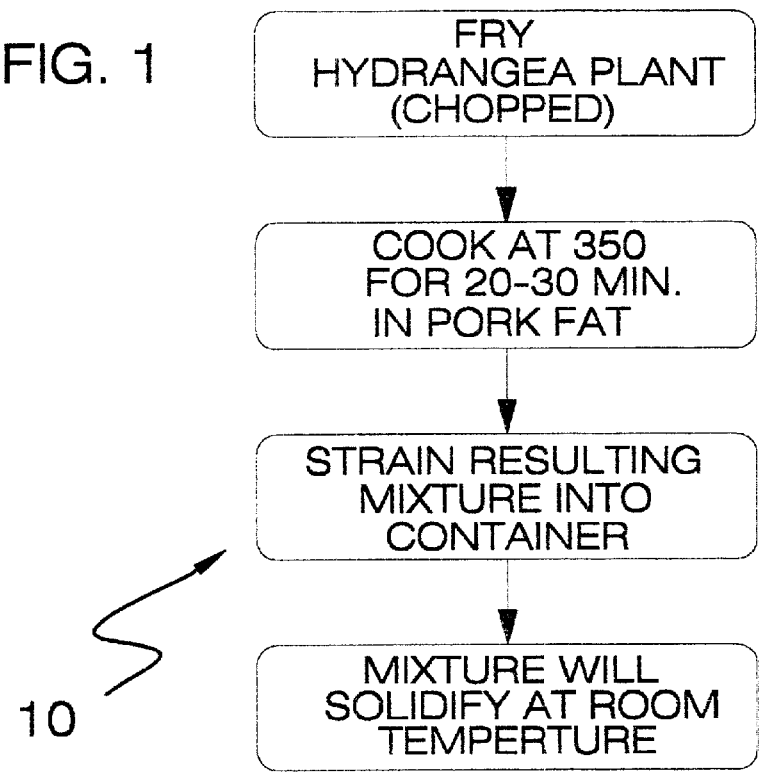
FIG. 1 is a schematic flow diagram of a method of making a new salve for treating burns according to the present invention.
Figure 2:
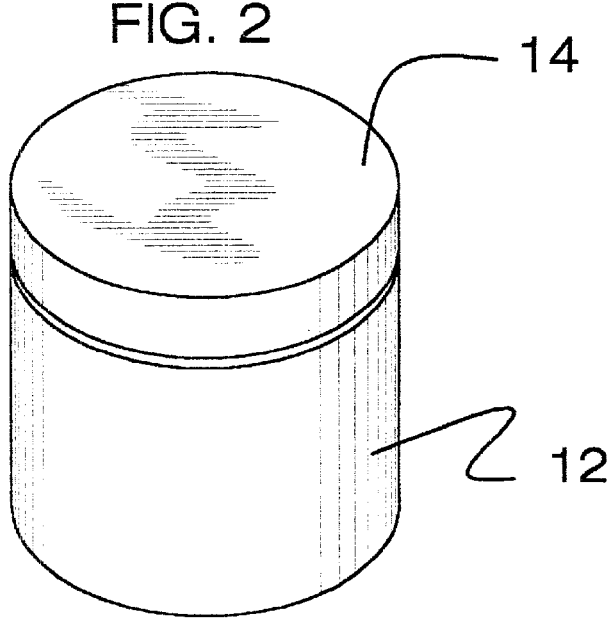
FIG. 2 is a schematic perspective view of a container of the present invention.

With reference now to the drawings, and in particular to FIGS. 1 and 2 thereof, a new salve for treating burns embodying the principles and concepts of the present invention and generally designated by the reference numeral 10 will be described.

As best illustrated in FIGS. 1 and 2, the method of making salve for treating burns 10 generally comprises the following steps:

1. Step 1. Heat 3 pounds of pork fat. The pork fat should be non-salted.
2. Step 2. Chop 2 pounds of hydrangea plant.
3. Step 3. Mix the chopped hydrangea plant with the pork fat to form a mixture.
4. Step 4. Fry the mixture for 25 minutes or until the hydrangea plant has turned brown. Alternatively, the mixture may be baked at a temperature of 175 degrees Celsius for approximately 20 minutes to 30 minutes.
5. Step 5. Pour the mixture through a strainer to define a strained mixture.
6. Step 6. Collecting the strained mixture in a container 12.
7. Step 7. Cooling the strained mixture to a temperature less than 35 degrees Celsius such that the strained mixture solidifies.
8. Step 8. Covering the container with a cover 14.

In use once solidified the mixture forms a salve which is spread over a burn area of a person. The salve serves to offer a cooling effect, reduces pain and scarring and promotes recovery.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A method of making a salve for treating burns comprising the steps of combining 3 parts of pork fat with 2 parts of chopped Hydrangea plant by weight to form a mixture;

heating said mixture at a temperature of 175 degrees Celsius until said hydrangea plant has turned brown;

straining said mixture to define a strained mixture; and cooling said strained mixture to a temperature less than 35 degrees Celsius such that said strained mixture solidifies.

2. The method of making a salve for treating burns as in claim 1, wherein the step of heating said mixture comprises the step of frying said mixture.

3. The method of making a salve for treating burns as in claim 1, wherein the step of heating said mixture comprises the step of baking said mixture.

4. The method of making a salve for treating burns as in claim 1, further including the step of collecting said mixture in a container before cooling said strained mixture; and covering said container with a lid.

5. A method of making a salve for treating burns comprising the steps of heating 3 pounds of pork fat;

chopping 2 pounds of Hydrangea plant;

mixing said chopped Hydrangea plant with said pork fat to form a mixture;

frying said mixture for 25 minutes or until said Hydrangea plant has turned brown;

pouring said mixture through a strainer to define a strained mixture;

collecting said strained mixture in a container; and cooling said strained mixture to a temperature less than 35 degrees Celsius such that said strained mixture solidifies.

6. A salve for treating burns comprising 3 pounds of pork fat;

2 pounds of chopped Hydrangea plant;

wherein said chopped Hydrangea plant is mixed with said pork fat to form a mixture, wherein said mixture is cooked at a temperature of 175 degrees Celsius until said Hydrangea plant has turned brown, wherein said mixture is strained to define a strained mixture and collected in a container such that said strained mixture may cool and solidify.

* * * * *